(12) United States Patent
Yang et al.

(10) Patent No.: US 11,984,220 B2
(45) Date of Patent: May 14, 2024

(54) VIRTUAL CONSULTATION METHOD AND ELECTRONIC DEVICE

(71) Applicants: KURA Care LLC, San Diego, CA (US); KURA Med Inc., Taipei (TW)

(72) Inventors: Kai-Chieh Yang, San Diego, CA (US); Chih-Wei Chiu, Kaohsiung (TW); Alvin Hsu, San Diego, CA (US)

(73) Assignees: KURA CARE LLC, San Diego, CA (US); KURA MED INC., Taipei (TW)

( * ) Notice: Subject to any disclaimer, the term of this patent is extended or adjusted under 35 U.S.C. 154(b) by 504 days.

(21) Appl. No.: 16/681,849

(22) Filed: Nov. 13, 2019

(65) Prior Publication Data

US 2020/0203011 A1 Jun. 25, 2020

Related U.S. Application Data

(60) Provisional application No. 62/760,044, filed on Nov. 13, 2018.

(51) Int. Cl.
*G16H 40/67* (2018.01)
*G06Q 50/20* (2012.01)
*G16H 10/20* (2018.01)

(52) U.S. Cl.
CPC ............ *G16H 40/67* (2018.01); *G06Q 50/20* (2013.01); *G16H 10/20* (2018.01)

(58) Field of Classification Search
CPC ........ G16H 40/67; G16H 10/20; G16H 50/20; G16H 50/30; G16H 50/70; G06Q 50/20
See application file for complete search history.

(56) References Cited

U.S. PATENT DOCUMENTS

2017/0262609 A1* 9/2017 Perlroth ................. G16H 10/60
2017/0310886 A1 10/2017 Hurst
2018/0122509 A1* 5/2018 Christiansson ........ G16H 40/63

FOREIGN PATENT DOCUMENTS

CN 100416583 9/2008
WO WO-2016079506 A1 * 5/2016 ........... G06F 19/325

OTHER PUBLICATIONS

Chen, Yinpeng; Xu, Weiwei; Sundaram, Hari; Rikakis, Thanassis; Liu, Sheng Min. A Dynamic Decision Network Framework for Online Media Adaptation in Stroke Rehabilitation. ACM Transactions on Multimedia Computing Communications and Applications 5.1 Assoc Computing Machinery. (Oct. 2008) (Year: 2008).*
"Office Action of Taiwan Counterpart Application", issued on Jun. 2, 2020, p. 1-p. 5.

* cited by examiner

*Primary Examiner* — Linh Giang Le
(74) *Attorney, Agent, or Firm* — WPAT, PC

(57) ABSTRACT

A virtual consultation method and an electronic device are provided. The method includes: receiving physiological information obtained through sensing a user by a sensing device; analyzing the physiological information to obtain an analysis result; adjusting weights of a plurality of questions according to the analysis result and determining a first question applicable to the user and an order of the first question according to the weights; and outputting the first question according to the order to simulate a question asked by a doctor for the user during consultation.

14 Claims, 2 Drawing Sheets

VIRTUAL CONSULTATION METHOD AND ELECTRONIC DEVICE

CROSS REFERENCE TO RELATED APPLICATION

This application claims the priority benefit of U.S. provisional application Ser. No. 62/760,044, filed on Nov. 13, 2018. The entirety of the above-mentioned patent application is hereby incorporated by reference herein and made a part of specification.

BACKGROUND

Technical Field

The disclosure relates to a virtual consultation method and an electronic device.

Description of Related Art

Generally, patients with chronic conditions need home care and condition tracking after discharge. Nevertheless, a doctor cannot track physiological information of a patient on a daily basis. Taking a patient with heart failure as an example, a doctor is not able to monitor heart rate in the patient's daily life and cannot get updates on the symptoms reported by the patient without face-to-face visit. Further, the doctor cannot evaluate whether the patient suffers from an adverse drug effect or other side effects caused by a new drug after a medication change, and cannot know whether the patient has taken medicine on a regular basis either.

SUMMARY

The disclosure provides a virtual consultation method with use of an electronic device capable of simulating a question asked by healthcare professional, such as a doctor, physician, clinician and/or other medical personnel, for a patient during consultation. The disclosure provides a method for delivering virtual consultation by improving post-acute monitoring efficacy and caring quality for a user, with use of an electronic device, to simulate a face-to-face visit scenario between a healthcare professional and the user.

The disclosure provides a virtual consultation method for an electronic device, and the method includes the following steps. Physiological information of a user is received via an output/input device, wherein the physiological information is acquired by a sensing device configured to monitor at least one physiological condition of the user. The physiological information is analyzed via a processor to obtain an analysis result. Weights of a plurality of questions are adjusted via the processor based on the analysis result and at least one question applicable to the user and an order of the at least one question are determined based on the weights. The at least one question is outputted via the output/input device based on the order to simulate a question that a healthcare professional might ask during consultation.

The disclosure further provides an electronic device including an output/input device and a processor. The processor is coupled to the output/input device. The output/input device receives physiological information of a user, wherein the physiological information is acquired by a sensing device configured to monitor at least one physiological condition of the user. The processor analyzes the physiological information to obtain an analysis result. The processor adjusts weights of a plurality of questions based on the analysis result and determines at least one question applicable to the user and an order of the at least one question based on the weights. The output/input device outputs the at least one question based on the order to simulate a question that a healthcare professional might ask the user during consultation.

To sum up, in the virtual consultation method and the electronic device provided by the disclosure, the physiological information may be obtained through an existing remote instrument, and the questions applicable to the user may be outputted based on the analysis result of the physiological information, so that the questions raised by the doctor for the user during consultation may be simulated.

DESCRIPTION OF THE EMBODIMENTS

Figure 1:
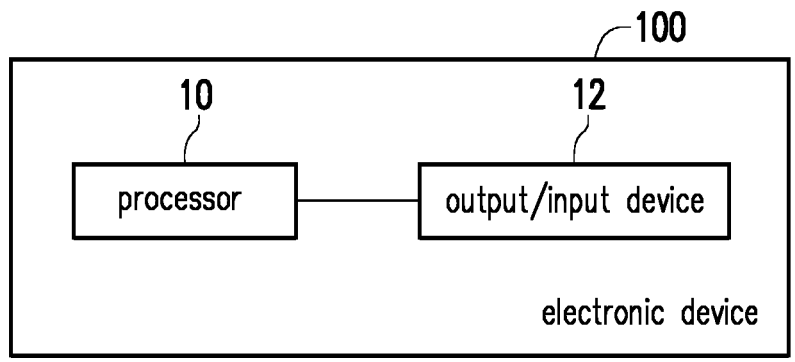
FIG. 1 is a block view of an electronic device according to an embodiment of the disclosure.

FIG. 1 is a block view of an electronic device according to an embodiment of the disclosure.

With reference to FIG. 1, an electronic device 100 may be, but not limited to, a computing device, such as a smartphone, a tablet computer, a notebook computer, a personal computer, a smartwatch, a smart bracelet, a smart-speaker, smart-earbuds, a biosensor and the like.

The electronic device 100 may include a processor 10, an input/output circuit 12, and a storage device (not shown). The input/output circuit 12 and the storage device are coupled to the processor 10. In addition, the electronic device 100 may also include other elements, such as a communication chip, which is not limited herein.

The processor 10 may be a central processing unit (CPU) or other programmable microprocessor for general or special use, a digital signal processor (DSP), a programmable controller, an application specific integrated circuit (ASIC), or any other similar devices or a combination of the foregoing devices.

The input/output circuit 12 may be a circuit configured for receiving a signal or a file and may transmit the received signal or file to the processor 10. In addition, the input/output circuit 12 may also be configured for receiving a signal or a file generated by the processor 10 and outputs such signal or file to other interfaces or devices.

The storage device may be a fixed or a movable random access memory (RAM) in any form, a read-only memory (ROM), a flash memory, a hard disk drive (HDD), a solid state drive (SSD), any other similar devices, or a combination of the foregoing devices.

In this embodiment, a plurality of program code snippets are stored in the storage device of the electronic device 100, and the program code snippets are executed by the processor 10 of the electronic device 100 after being installed. For instance, the storage device of the electronic device 100 includes a plurality of modules. Operations applied in the electronic device 100 are respectively executed through the modules, and each of the modules is formed by one or plural program code snippets. Nevertheless, the disclosure is not limited thereto, and the operations may also be implemented through using other hardware forms.

Figure 2:
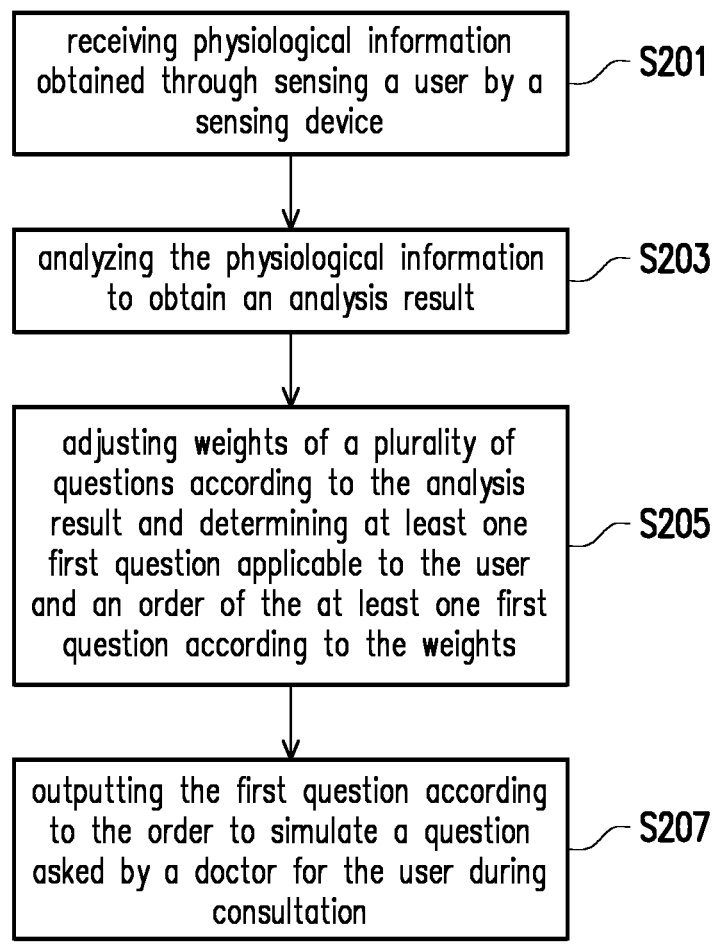
FIG. 2 is a flow chart of a virtual consultation method according to an embodiment of the disclosure.

FIG. 2 is a flow chart of a virtual consultation method according to an embodiment of the disclosure.

With reference to FIG. 2, in this embodiment, a user may wear a sensing device, which is adapted to sense, monitor, measure and/or detect his/her physiological condition to obtain physiological information. An output/input device 12 receives the physiological information obtained through sensing the user by the sensing device (step S201). The physiological information may be, but not limited to, heart rate, respiration rate, stress level, blood pressure, body temperature, ECG signal, PPG signal and the like. Nevertheless, the disclosure is not intended to limit any content or scope of the physiological information. The sensing device may be an existing hardware device, such as a smart bracelet, an electrocardiograph, and the like, which is not limited herein. Alternatively, the sensing device may also be a built-in sensor of a smartphone, such as an accelerator, an altimeter, a GPS, or a front or rear lens, or may be a sensor equipped with any other apparatus, which is not limited herein.

Next, the processor 10, via inputting the physiological information in a model described below, may analyze the received physiological information to obtain an analysis result (step S203). The processor adjusts weights of a plurality of questions according to the analysis result through the model, and determines a question (aka a first question) applicable to the user and an order of the first question based on the weights (step S205). That is, in the disclosure, content and order of the questions applicable to the user are dynamically adjusted and/or chosen, and therefore a personalized question set or questionnaire related to the underlying physiological condition is accordingly generated.

In particular, in step S205, the processor 10 may also obtain, via the output/input device, answer content (aka second answer content) previously filled in by the user and corresponding to another question (aka a second question) and an order of the second question through the output/input device 12. The processor 10 adjusts the weights of the plurality of questions according to the analysis result, the second answer content, and the order of the second question and determines the first question applicable to the user and the order of the first question based on the weights.

Figure 3:
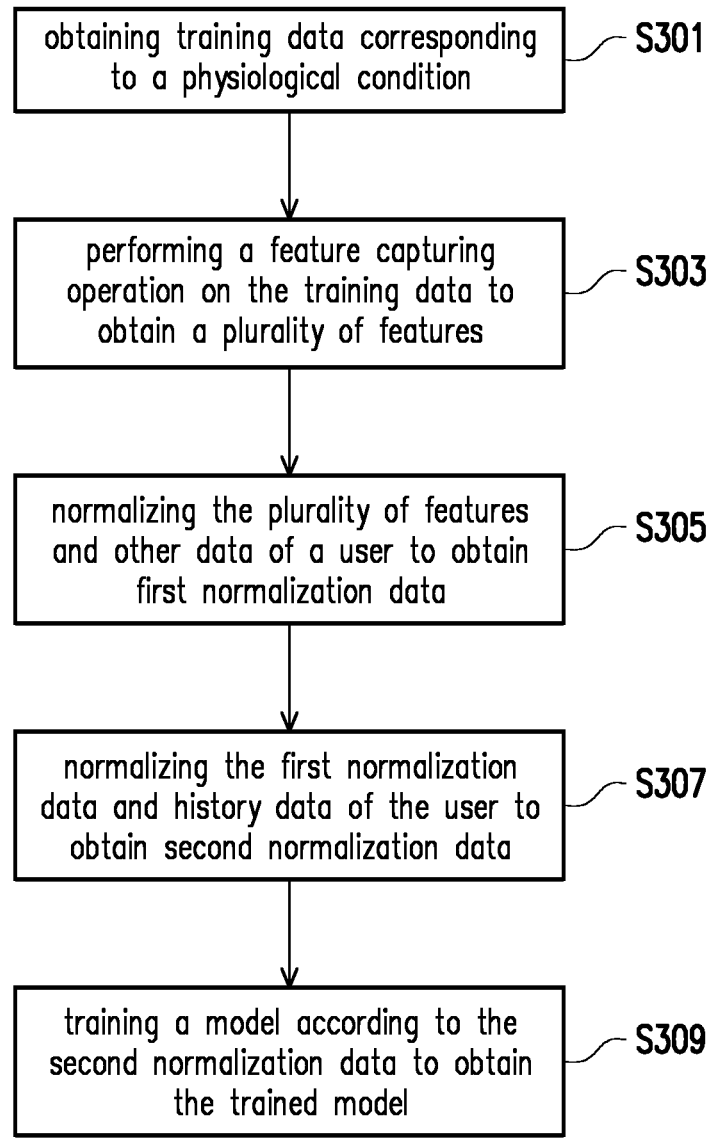
FIG. 3 is a flow chart showing a process of training a model according to an embodiment of the disclosure.

FIG. 3 is a flow chart showing a process of training a model according to an embodiment of the disclosure.

With reference to FIG. 3, the flow chart is configured to describe how to build the aforementioned model. First, the processor gathers training data of physiological condition(s) based on the user's physiological information (step S301). The training data may include, but is not limited to, the physiological information (e.g., a numerical value) associated with the physiological condition, the meaning of the numerical value, a normal range and an abnormal range of the numerical value, etc. In addition, the training data may further include, but is not limited to, a question about a medical triage mechanism. Moreover, during the model training process, a relationship between a question and the physiological information may be marked in advance to facilitate subsequent trainings.

Next, the processor 10 performs a feature extraction operation on the training data to obtain a plurality of features (step S303). The feature extraction operation may be carried out through a conventional machine learning method, which is not provided herein. The processor 10 normalizes the plurality of features and other data of other users to obtain first normalization data (step S305). The processor 10 normalizes the first normalization data along with the history data (such as prior physiological data, prior medication data and the like) from the user to obtain second normalization data (step S307). Finally, the processor 10 trains the model based on the second normalization data to obtain the trained model (step S309). Model training may be learned from the prior art, which is not provided herein.

Note that in step S307, the first normalization data in combination with the history data inputted from the user himself/herself are normalized, and in this way, a user specific output corresponding to the different user may be created accordingly. For instance, if a user is experiencing a chronic condition of high blood pressure, his blood pressure readings are usually above the normal range. After step S307 is performed, a range of his habitual blood pressure is included, and a warning is provided or a risk level is increased only when the measured blood pressure exceeds this range. As such, the user is prevented from being frequently provided with a warning due to his relatively high blood pressure.

With reference to FIG. 2 again, after step S205 is performed, the output/input device 12 outputs the first question according to the order determined in step S205, so as to simulate a question asked by a doctor for the user during consultation (step S207).

In addition, when receiving the first question, the user may answer (or respond to) the first question. The processor 10 may obtain first answer content from the user in response to the first question through the output/input device 12. The processor 10 then determines the risk level (and the like) associated with a physiological condition based on the first answer content. The output/input device 12 outputs an output message corresponding to the risk level. For instance, when the first question is related to a heart disease, the physiological condition may be assessed through measurements of blood pressure or heart rate, and the risk level may be configured to be an indicator presenting blood pressure or heart rate. Taking blood pressure as an example, when the risk level of blood pressure is relatively high (e.g., higher than a threshold), an output message corresponding to the blood pressure may be presented in red as a warning. On the contrary, when the risk level of the blood pressure is relatively low (e.g., lower than the threshold), the output message corresponding to the blood pressure may be presented in green. In an embodiment, when the output message includes various physiological conditions, the physiological conditions may be sorted according to the severity (high and low levels) of risk levels associated with the physiological conditions. For instance, the risk levels may be ranked from high to low to facilitate observation made by the user or the doctor.

In another embodiment, particularly, an integrated report for a patient or an extensive subject may be provided through a semi-automatic, manual, or full automatic manner according to the output message. Firstly, in the semi-automatic manner, the medical staff may verify the correctness of contents of the output message, including "full smart mode interpretation" and "overall report and details" provided by the model (aka an artificial smart engine), and provide "integrated disease interpretation" to the patient. At this stage, the model may also perform learning based on the feedbacks provided by the medical staff.

Secondly, in the manual manner, the medical staff may provide the "integrated disease interpretation" to the patient with reference to the output message including the "full smart mode interpretation" and "overall report and details" provided by the model and may intervene moderately. For instance, after learning about medication use of the patient, the medical staff may provide suggestions about lifestyle adjustment, initiate an early return visit, and adjust medication to reduce adverse drug reactions or side effects. At this stage, the model may also perform learning based on the feedbacks provided by the medical staff.

Lastly, in the full automatic manner, the output messages of the "full smart mode interpretation" and "overall report and details" as well as the "integrated disease interpretation" are automatically provided to the user through the model instead of the medical staff. In addition, the model may provide an early warning in a full smart mode, and such warning may further be provided to: a relatively healthy person having a higher risk, such as a family member of the patient (due to family medical history). For the general public, preventive tracking may also be performed.

In view of the foregoing disclosure, in the virtual consultation method and the electronic device, the physiological information may be obtained through an existing remote instrument, and the questions applicable to the user may be outputted according to the analysis result of the physiological information, so that the questions raised by the doctor for the user during consultation may be simulated. As a result, early prevention of diseases, lowered fatality rate, reduced nursing care costs, and other effects may be achieved through the method and the electronic device provided by the disclosure.

What is claimed is:

1. A virtual consultation method for an electronic device having a processor and an output/input device, the method comprising the steps of:
   receiving, via the output/input device, physiological information of a user automatically, wherein the physiological information is acquired by a sensing device configured to monitor at least one physiological condition of the user without requiring any action or input by the user;
   determining, via the processor, a customized measurement range for monitoring one of the at least one physiological condition of the user based on a history data of the user;
   obtaining, via the processor, training data of the at least one physiological condition based on the physiological information;
   performing, via the processor, a feature extraction operation on the training data to obtain a plurality of features;
   normalizing, via the processor, the plurality of features along with other data of other users to obtain a first normalization data;
   normalizing, via the processor, the first normalization data along with the history data of the user to obtain a second normalization data, the second normalization data being specifically normalized for only the user that the history data is based upon;
   training, via the processor, a model according to the second normalization data;
   analyzing, via the processor, the physiological information in conjunction with the model to obtain an analysis result;
   adjusting, via the processor, weights of a plurality of questions based on the analysis result and determining at least one question applicable to the user from the plurality of questions and determining an order of the at least one question for presentation to the user based on the adjusted weights; and
   outputting, via the output/input device, the at least one question based on the order thereby presenting a question for promoting interaction with the user during the virtual consultation by an emulated virtual healthcare provider.

2. The virtual consultation method as claimed in claim 1, further comprising the steps of:
   obtaining, via the output/input device, at least one answer content from the user in response to the at least one question;
   determining, via the processor, a risk level associated with each of the at least one physiological condition based on the at least one answer content; and
   outputting, via the output/input device, at least one output message corresponding to each risk level for the user.

3. The virtual consultation method as claimed in claim 1, wherein the method further comprises the steps of:
   obtaining, via the output/input device, at least one answer content from the user in response to the at least one question and the order of the at least one question; and
   adjusting, via the processor, the weights of the plurality of questions based on a combination of the analysis result, the at least one answer content, and the order of the at least one question and subsequentially determining at least one question other than the at least one question applicable to the user and an order of the at least one question other than the at least one question based on the adjusted weights.

4. The virtual consultation method as claimed in claim 1, wherein the step of analyzing the physiological information to obtain the analysis result further comprises:
   determining the at least one question applicable to the user based on the adjusted weights.

5. The virtual consultation method as claimed in claim 4, wherein training the model according to the second normalization data occurs before the step of analyzing the physiological information in conjunction with the model to obtain the analysis result.

6. An electronic device for conducting a virtual consultation method, the electronic device comprising:
   an output/input circuit; and
   a processor, coupled to the output/input circuit, wherein the output/input circuit receives physiological information of a user automatically, wherein the physiological information is acquired by a hardware sensor sensing device configured to monitor at least one physiological condition of the user without requiring any action or input by the user,
   the processor determines a customized measurement range for monitoring one of the at least one physiological condition of the user based on a history data of the user;
   the processor obtains training data of the at least one physiological condition based on the physiological information;
   the processor performs a feature extraction operation on the training data to obtain a plurality of features;
   the processor normalizes the plurality of features along with other data of other users to obtain a first normalization data;
   the processor normalizes the first normalization data along with the history data of the user to obtain a second normalization data, the second normalization data being specifically normalized for only the user that the history data is based upon;
   the processor trains a model according to the second normalization data;
   the processor analyzes the physiological information in conjunction with the model to obtain an analysis result, the processor adjusts weights of a plurality of questions based on the analysis result and determines at least one question applicable to the user from the plurality of questions and determining an order of the at least one question for presentation to the user based on the adjusted weights, and the output/input circuit outputs the at least one question based on the order thereby presenting a question for promoting interaction with the user during the virtual consultation by an emulated virtual healthcare provider.

7. The electronic device as claimed in claim 6, wherein the processor obtains, via the output/input circuit, at least one answer content from the user in response to the at least one question, the processor determines a risk level associated with each of the at least one physiological condition based on the at least one answer content, and the output/input circuit outputs at least one output message corresponding to each risk level for the user.

8. The electronic device as claimed in claim 6, wherein the processor obtains, via the output/input circuit, at least one answer content from the user in response to the at least one question and the order of the at least one question, and the processor adjusts the weights of the plurality of questions based on a combination of the analysis result, the at least one answer content, and the order of the at least one question and subsequentially determines at least one question other than the at least one question applicable to the user and an order of the at least one question other than the at least one question based on the adjusted weights.

9. The electronic device as claimed in claim 6, wherein, in the operation of analyzing the physiological information to obtain the analysis result, the processor determines the at least one question applicable to the user based on the adjusted weights.

10. The electronic device as claimed in claim 9, wherein training the model according to the second normalization data occurs before the operation of analyzing the physiological information in conjunction with the model to obtain the analysis results.

11. The virtual consultation method as claimed in claim 2, wherein when the at least one output message includes a plurality of physiological conditions, sorting the physiological conditions, via the processor, according to the risk levels of the physiological conditions.

12. The virtual consultation method as claimed in claim 2, wherein the method further comprises the steps of:

outputting, via the output/input device, an integrated report comprising the at least one output message.

13. The electronic device as claimed in claim 7, wherein when the at least one output message includes a plurality of physiological conditions, the processor sorts the physiological conditions according to the risk levels of the physiological conditions.

14. The electronic device as claimed in claim 7, wherein the output/input circuit device outputs an integrated report comprising the at least one output message.

* * * * *